(12) United States Patent
Gizurarson

(10) Patent No.: US 8,217,033 B2
(45) Date of Patent: Jul. 10, 2012

(54) METHODS AND COMPOSITIONS FOR THE DELIVERY OF A THERAPEUTIC AGENT

(75) Inventor: Sveinbjorn Gizurarson, Reykjavik (IS)

(73) Assignees: Hananja EHF, Reyjavik (IS); University of Iceland, Reykjavik (IS)

( * ) Notice: Subject to any disclaimer, the term of this patent is extended or adjusted under 35 U.S.C. 154(b) by 0 days.

(21) Appl. No.: 12/469,448

(22) Filed: May 20, 2009

(65) Prior Publication Data

US 2009/0227568 A1 Sep. 10, 2009

Related U.S. Application Data

(63) Continuation of application No. 12/016,724, filed on Jan. 18, 2008.

(30) Foreign Application Priority Data

Jan. 19, 2007 (IS) .................................. 8593/2007

(51) Int. Cl.
*A61K 31/55* (2006.01)
(52) U.S. Cl. .................................................. 514/220
(58) Field of Classification Search .................... None
See application file for complete search history.

(56) References Cited

U.S. PATENT DOCUMENTS

| | | | |
|---|---|---|---|
| 3,812,853 A | 5/1974 | Crain | |
| 4,153,689 A | 5/1979 | Hirai et al. | |
| 4,464,378 A | 8/1984 | Hussain | |
| 4,673,679 A | 6/1987 | Aungst et al. | |
| 4,782,047 A | 11/1988 | Benjamin et al. | |
| 4,863,720 A | 9/1989 | Burghart et al. | |
| 4,889,860 A | 12/1989 | Rzeszotarski et al. | |
| 4,946,069 A | 8/1990 | Fuchs et al. | |
| 4,950,664 A | 8/1990 | Goldberg | |
| 4,973,596 A | 11/1990 | Cohen | |
| 5,132,114 A | 7/1992 | Stanley et al. | |
| 5,166,202 A | 11/1992 | Schweizer | |
| 5,169,029 A | 12/1992 | Behar et al. | |
| 5,225,183 A | 7/1993 | Purewal et al. | |
| 5,307,953 A | 5/1994 | Regan et al. | |
| 5,369,095 A | 11/1994 | Kee et al. | |
| 5,393,773 A | 2/1995 | Craig et al. | |
| 5,397,771 A | 3/1995 | Bechgaard et al. | |
| 5,428,006 A | 6/1995 | Bechgaard et al. | |
| 5,457,100 A | 10/1995 | Daniel | |
| 5,474,759 A | 12/1995 | Fassberg et al. | |
| 5,529,787 A | 6/1996 | Merrill et al. | |
| 5,543,434 A | 8/1996 | Weg | |
| 5,554,639 A | 9/1996 | Craig et al. | |
| 5,577,497 A | 11/1996 | Mecikalski et al. | |
| 5,622,166 A | 4/1997 | Eisele et al. | |
| 5,629,011 A | 5/1997 | Illum et al. | |
| 5,637,314 A | 6/1997 | Sharpe et al. | |
| 5,683,677 A | 11/1997 | Purewal et al. | |
| 5,693,608 A | 12/1997 | Bechgaard et al. | |
| 5,695,743 A | 12/1997 | Purewal et al. | |
| 5,702,725 A | 12/1997 | Merrill et al. | |
| 5,705,520 A | 1/1998 | Craig et al. | |
| 5,766,573 A | 6/1998 | Purewal et al. | |
| 5,789,375 A | 8/1998 | Mukae et al. | |
| 5,855,907 A | 1/1999 | Peyman | |
| 5,866,143 A | 2/1999 | Elkhoury | |
| 5,897,858 A | 4/1999 | Haslwanter et al. | |
| 5,948,389 A | 9/1999 | Stein | |
| 5,958,379 A | 9/1999 | Regenold et al. | |
| 6,007,834 A | 12/1999 | Merkus | |
| 6,013,632 A | 1/2000 | Jones et al. | |
| 6,015,797 A | 1/2000 | Camborde et al. | |
| 6,017,963 A | 1/2000 | Alfonso et al. | |
| RE36,744 E | 6/2000 | Goldberg | |
| 6,110,486 A | 8/2000 | Dugger, III | |
| 6,193,984 B1 | 2/2001 | Ghiasi et al. | |
| 6,193,985 B1 | 2/2001 | Sonne et al. | |
| 6,228,383 B1 | 5/2001 | Hansen et al. | |
| 6,234,366 B1 | 5/2001 | Fuchs et al. | |
| 6,255,502 B1 | 7/2001 | Penkler et al. | |
| 6,274,635 B1 | 8/2001 | Travis | |
| 6,274,653 B1 | 8/2001 | Hecht et al. | |
| 6,514,482 B1 | 2/2003 | Bartus et al. | |
| 6,528,465 B1 | 3/2003 | Cantoro | |
| 6,565,832 B1 | 5/2003 | Haslwanter et al. | |
| 6,565,841 B1 | 5/2003 | Niven et al. | |
| 6,608,073 B1 | 8/2003 | Hussain et al. | |
| 6,610,271 B2 | 8/2003 | Wermeling | |
| 6,613,308 B2 | 9/2003 | Bartus et al. | |

(Continued)

FOREIGN PATENT DOCUMENTS

EP 0519351 12/1992

(Continued)

OTHER PUBLICATIONS

The Dow Chemical Company (PEGs & MPEGs, Mar. 2006).*
Weber et al., "Premedication with nasal s-ketamine and midazolam provides good conditions for induction of anesthesia in preschool children" *Can. J. Anesth.* (2003) 50, pp. 470-475.
Patent Cooperation Treaty (PCT) International Search Report; International Application No. PCT/US05/08090, completed Jun. 12, 2005 and mailed Jun. 30, 2005 (2 pages).
Knoester, P.D. et al., "Pharmacokinetics and pharmacodynamics of midazolam administered as a concentrated intranasal spray. A study in healthy volunteers" *Br. J. Clin. Pharmacol.* (2002); 53(5), pp. 501-507.
Bechgaard, E. et al., "Solubilization of various benzodiazepines for intranasal administration, a pilot study" *Pharm. Dev. Technol.* (1997); 2(3), pp. 293-296.
Hjortkjaer, R.K. et al., "Single- and repeated-dose local toxicity in the nasal cavity of rabbits after intranasal adminstration of different glycols for formulations containing benzodiazepines" *J. Pharm. Pharmacol.* (1999); 51(4), pp. 377-383.

(Continued)

*Primary Examiner* — Brandon Fetterolf
*Assistant Examiner* — Craig Ricci
(74) *Attorney, Agent, or Firm* — Kagan Binder, PLLC

(57) ABSTRACT

The present invention provides a liquid pharmaceutical composition comprising a therapeutic agent and an alkoxy-polyethylene glycol, for example, methoxy-polyethylene glycol, for administration of the therapeutic agent to the mammal. The compositions can be applied to a membrane, for example, a nasal membrane during intranasal administration. The invention also provides methods of administering such compositions to a mammal.

21 Claims, No Drawings

U.S. PATENT DOCUMENTS

| | | | |
|---|---|---|---|
| 6,627,211 | B1 | 9/2003 | Choi et al. |
| 6,737,043 | B2 | 5/2004 | Rabinowitz et al. |
| 6,805,853 | B2 | 10/2004 | Rabinowitz et al. |
| 6,936,605 | B2 | 8/2005 | March |
| 6,977,070 | B2 | 12/2005 | Dugger, III |
| 6,979,437 | B2 | 12/2005 | Bartus et al. |
| 7,018,619 | B2 | 3/2006 | Rabinowitz et al. |
| 7,045,119 | B2 | 5/2006 | Rabinowitz et al. |
| 7,060,255 | B2 | 6/2006 | Rabinowitz et al. |
| 7,070,765 | B2 | 7/2006 | Rabinowitz et al. |
| 7,087,218 | B2 | 8/2006 | Rabinowitz et al. |
| 7,090,830 | B2 | 8/2006 | Hale et al. |
| 7,132,112 | B2 | 11/2006 | Choi et al. |
| 7,449,173 | B2 | 11/2008 | Rabinowitz et al. |
| 7,470,421 | B2 | 12/2008 | Rabinowitz et al. |
| 7,645,442 | B2 | 1/2010 | Hale et al. |
| 7,700,588 | B2 | 4/2010 | Merkus |
| 2002/0037319 | A1 | 3/2002 | Drizen et al. |
| 2003/0012738 | A1 | 1/2003 | Rabinowitz et al. |
| 2003/0077300 | A1 | 4/2003 | Wermeling |
| 2003/0134811 | A1 | 7/2003 | Jackson et al. |
| 2003/0163099 | A1 | 8/2003 | Wermeling et al. |
| 2003/0171439 | A1 | 9/2003 | Lawyer et al. |
| 2003/0175354 | A1 | 9/2003 | Drizen et al. |
| 2003/0206867 | A1 | 11/2003 | Wermeling |
| 2004/0115133 | A1 | 6/2004 | Wermeling |
| 2004/0166158 | A1 | 8/2004 | Davis et al. |
| 2004/0176359 | A1 | 9/2004 | Wermeling |
| 2004/0185003 | A1 | 9/2004 | Rabinowitz et al. |
| 2005/0137164 | A1 | 6/2005 | Arkin et al. |
| 2005/0153956 | A1 | 7/2005 | Merkus |
| 2005/0244517 | A1 | 11/2005 | Hall et al. |
| 2006/0110415 | A1 | 5/2006 | Gupta |
| 2006/0116350 | A1 | 6/2006 | Pasricha et al. |
| 2006/0147386 | A1 | 7/2006 | Wermeling |
| 2006/0198896 | A1 | 9/2006 | Liversidge et al. |
| 2006/0210614 | A1 | 9/2006 | Quay et al. |
| 2007/0208011 | A1 | 9/2007 | Cloyd et al. |
| 2007/0212307 | A1 | 9/2007 | Wermeling et al. |
| 2008/0070904 | A1 | 3/2008 | Jamieson et al. |
| 2008/0138383 | A1 | 6/2008 | Bortz et al. |
| 2008/0279784 | A1 | 11/2008 | Cartt et al. |
| 2009/0088421 | A1 | 4/2009 | Orr |
| 2009/0130216 | A1 | 5/2009 | Cartt et al. |
| 2009/0233912 | A1 | 9/2009 | Castile et al. |
| 2009/0304801 | A1 | 12/2009 | Liversidge et al. |

FOREIGN PATENT DOCUMENTS

| | | |
|---|---|---|
| EP | 0698388 | 2/1996 |
| EP | 0698388 B1 | 12/1999 |
| EP | 1703896 | 12/2008 |
| WO | WO-87/05210 | 9/1987 |
| WO | WO-90/02737 | 3/1990 |
| WO | 95/01414 | 1/1995 |
| WO | WO-95/01414 | 1/1995 |
| WO | WO-98/00152 | 1/1998 |
| WO | WO-99/21908 | 5/1999 |
| WO | WO-01/06987 | 2/2001 |
| WO | WO-01/12230 | 2/2001 |
| WO | WO-01/12718 | 2/2001 |
| WO | WO-2002/11778 | 2/2002 |
| WO | WO-2002/089751 | 11/2002 |
| WO | 03/101494 | 12/2003 |
| WO | WO-03/101494 | 12/2003 |
| WO | 2004/082589 | 9/2004 |
| WO | WO-2004/082589 A2 | 9/2004 |
| WO | WO-2005/020906 | 3/2005 |
| WO | WO-2005/067893 | 7/2005 |
| WO | WO 2005/067893 * | 7/2005 |
| WO | 2005/072826 | 8/2005 |
| WO | WO-2005/072826 A2 | 8/2005 |
| WO | 2006/119803 | 11/2006 |
| WO | WO-2006/119803 A1 | 11/2006 |
| WO | WO-2007/032962 | 3/2007 |
| WO | WO-2007/067761 | 6/2007 |
| WO | WO-2007/109141 | 9/2007 |
| WO | WO-2007/111933 | 10/2007 |
| WO | WO-2008/063634 | 5/2008 |
| WO | WO-2009/053741 | 4/2009 |

OTHER PUBLICATIONS

Björkman, S. et al., "Pharmacokinetics of midazolam given as an intranasal spray to adult surgical patients" Br. J. Anaesth. (1997); 79(5), pp. 575-580.

European Patent Office Supplementary Partial European Search Report; European Application No. EP05725332, completed Nov. 9, 2007.

Greenblatt, D. et al., "Pharmacokinetics and pharmacodynamics of single-dose triazolam: electroencephalography compared with digital symbol substitution test" Br. J. Clin. Pharmacol. (2005); 60, pp. 244-248.

Lahat, E. et al., "Comparison of intranasal midazolam with intravenous diazepam in treating febrile seizures in children: prospective randomized study" BMJ (2000); 321, pp. 83-86.

Kain, Z.N. et al., "Premedication in the United States: a status report." Anesth. Analg. (1997); 84, pp. 427-432.

Coda, B.A. et al., "Pharmacokinetics and bioavailability of single does intranasal hydromorphone hydrochloride in healthy volunteers" Anesth. Analg. (2003); 97, pp. 117-123.

Crankshaw et al., "The Effect of Solvents on the Potency of Chlordiazepoxide, Diazepam, Medazepam and Nitrazepam," J. Pharm. Pharmac., 1971, 23, pp. 313-321.

Lau, S.W.J. et al., "Absorbtion of Diazepam and Lorazepam Following Intranansal Administration" International Journal of Pharmaceutics (1989); 54, pp. 171-174.

Wermeling et al., "Pharmacokinetics and Pharmacodynamics of a New Intranasal Midazolam Formulation in Healthy Volunteers," International Anesthesia Research Society, vol. 103, No. 2, Aug. 2006, pp. 344-349.

Dale et al., "Intranasal Midazolam: A Comparison of Two Delivery Devices in Human Volunteers," Journal of Pharmacy and Pharmacology 2006, 58: pp. 1311-1318.

Morimoto et al., "Nasal Absorption of Nifedipine from Gel Preparations in Rats," Chem. Pharm. Bull., 35(7) pp. 3041-3044, (1987).

Wermeling et al., "Bioavailability and Pharmacokinetics of Lorazepam after Intranasal, Intravenous, and Intramuscular Administration." J. Clin. Pharmacol. 2001; 41; 1225, pp. 1225-1231.

Burstein et al., "Pharmacokinetics and Pharmacodynamics of Midazolam after Intranasal Administration," J. Clin. Pharmacol. 1997; 37: 711-718.

Loftsson et al., "Cyclodextrin Solubilization of Benzodiazepines: Formulation of Midazolam Nasal Spray," International Journal of Pharmaceutics 212 (2001) pp. 29-40.

Lacoste et al., "Intranasal Midazolam in Piglets: Pharmacodynamics (0.2 vs 0.4 mg/kg) and Pharmacokinetics (0.4 mg/kg) with Bioavailability Determination," Laboratory Animals Ltd. Laboratory Animals (2000) 34, pp. 29-35.

Dale et al., "Intranasal Midazolam: A comparison of Two Delivery Devices in Human Volunteers," PubMed, 1: J Pharm Pharmacol. Oct. 2006; 58(10): 1311-8. (abstract only).

Mazaheri et al., "Assessment of Intranasal Midazolam Administration with a Dose of 0.5 mg/kg in Behavior Management of Uncooperative Children," PubMed, 1: J Clin Pediatr Dent. 2008 Winter; 32(2): 95-9. (abstract only).

McIlwain et al., "Allergic Reaction to Intranasal Midazolam HCl: A Case Report," PubMed, 1: Pediatr Dent. Jul.-Aug. 2004; 26(4): 359-61. (abstract only).

Gilchrist et al., "The Use of Intranasal Midazolam in the Treatment of Paediatric Dental Patients," PubMed, 1: Anaesthesia. Dec. 2007; 62(12): 1262-5. (abstract only).

Gudmundsdottir et al., "Intranasal Administration of Midazolam in a Cyclodextrin Based Formulation: Bioavailability and Clinical Evaluation in Humans," PubMed, 1: Pharmazie. Dec. 2001; 56(12): 963-6. (abstract only).

Lloyd et al., "Intranasal Midazolam as an Alternative to General Anaesthesia in the Management of Children with Oral and Maxillofacial Trauma," PubMed, 1: Br J Oral Maxillofac Surg. Dec. 2000; 38(6): 593-595. (abstract only).

Scheepers et al., "Midazolam via the Intranasal Route: An Effective Rescue Medication for Severe Epilepsy in Adults with Learning Disability," PubMed, 1: Seizure. Dec. 1998; 7(6): 509-12. (abstract only).

Dallman et al., "Comparing the Safety, Efficacy and Recovery of Intranasal Midazolam vs. Oral Chloral Hydrate and Promethazine," PubMed, 1: Pediatr Dent. Sep.-Oct. 2001; 23(5): 424-30. (abstract only).

Vesal et al., "Clinical Evaluation of Intranasal Benzodiazepines, Alpha-Agonists and Their Antagonists in Canaries," PubMed, 1: Vet Anaesth Analg. May 2006; 33(3): 143-8. (abstract only).

Karst et al., "Auricular Acupuncture for Dental Anxiety: A Randomized Controlled Trial," PubMed, 1: Anesth Analg. Feb. 2007; 104(2): 295-300. (abstract only).

Wilson et al., "Nasal/Buccal Midazolam Use in the Community," PubMed, 1: Arch Dis Child. Jan. 2004; 89(1): 50-1. (abstract only).

Kupietzky et al., "Intranasal Midazolam Better at Effecting Amnesia after Sedation than Oral Hydroxyzine: A Pilot Study," PubMed, 1: Pediatr Dent. Jan.-Feb. 1996; 18(1): 32-4. (abstract only).

Kaufman et al., "Comparison Between Intranasal and Intravenous Midazolam Sedation (with or without patient control) in a Dental Phobia Clinic," PubMed, 1: J Oral Maxillofac Surg. Aug. 1994; 52(8): 840-3; discussion 844. (abstract only).

Fuks et al., "Assessment of Two Doses of Intranasal Midazolam for Sedation of Young Pediatric Dental Patients," PubMed, 1: Pediatr Dent. Jul.-Aug. 1994; 16(4): 301-5. (abstract only).

Abrams et al., "Safety and Effectiveness of Intranasal Administration of Sedative Medications (ketamine, midazolam, or sufentanil) for Urgent Brief Pediatric Dental Procedures," PubMed, 1: Anesth Prog. 1993; 40(3): 63-6. (abstract only).

Karabas et al., "Probing for Nasolacrimal Duct Obstruction Using Intranasal Midazolam Sedation as an Alternative to General Anesthesia," PubMed, 1: J Pediatr Ophthalmol Strabismuc. Mar.-Apr. 2006; 43(2): 79-84; quiz 100-1.

Wilton et al., "Preanesthetic Sedation of Preschool Children Using Intranasal Midazolam," Clinical Report, Anesthesiology, vol. 69, No. 6, Dec. 1988,pp. 972-975.

Patent Cooperation Treaty (PCT) International Search Report and Written Opinion: International Application No. PCT/US2008/051466, completed Dec. 1, 2008 and mailed Dec. 17, 2008 (11 pages).

Burstein et al., "Intranasal Midazolam Plasma Concentration Profile and Its Effect on Anxiety Associated with Dental Procedures," Anesth Prog (1996) 43: pp. 52-57.

Rey et al., "Pharmacokinetics of Midazolam in Children: Comparative Study of Intranasal and Intravenous Administration," European Journal of Clinical Pharmacology, (1991) 41: pp. 355-357.

Walberg et al., "Plasma Concentrations of Midazolam in Children Following Intranasal Administration," Anesthesiology, (1991) 74: pp. 233-235.

Methocel Cellulose Ethers Technical Handbook, Dow Chemical Company (32 pages), Sep. 2002.

Carbowax MPEG 350 & 350E Kinematic Viscosity Report, Dow Chemical Company (1 page), Sep. 2009.

Carbowax MPEG 500E & 550 Kinematic Viscosity Report, Dow Chemical Company (1 page), Sep. 2009.

Lui et al., "Intranasal Aborption of Flurazepam, Midazolam and Triazolam in Dogs," *J. Pharm. Sci.* 80: 1125-1129 (1991).

Ivaturi et al., Acta Neurol Scand. 2009, 120:353-357.

Costantino et al., International Journal of Pharmaceutics, 2007, vol. 337, pp. 1-24.

Bhattacharyya et al., Pediatr Neurol 2006 34:355-359.

de Haan et al., Epilepsia, 2010, 51(13):478-482.

Fisgin et al., J. Child Neurol. 2000, 833-835.

Fisgin et al., Journ. of Child Neurology. 2002, 17(2):123-126.

Harbord et al., J. Paediatr. Child Health. 2004, 40:556-558.

Holsti et al., Pediatric Emergency Care. 2007, 23(3):148-153.

Jeannet et al., Euro. Journ. of Paediatric Neurology. 1999, 3:73-77.

Kutlu et al., Brain & Develop. 2000, 22:359-361.

Kyrkou et al., Journ. of Intellec. & Develop. Disability. 2006, 31(3):131-138.

Mahmoudian et al., Epilepsy & Behavior. 2004. 5:253-255.

O'Regan et al., Develop. Medicine & Child Neurology. 1996, 38:1037-1045.

Scheepers et al., Seizure, 2000, 9:417-422.

Wermeling et al., Epilepsy Research, 2009, 83:124-132.

Aurora, Drug Delivery Technology, vol. 2 No. 7 (2002), pp. 1-8.

Harris et al., Journal of Pharmaceutical Sciences, vol. 78 (1989), pp. 470-471.

Illum et al., Journal of Aerosol Medicine, vol. 19 (2006), pp. 92-99.

Kilian et al., International Journal of Pharmaceutics, vol. 163 (1998), pp. 211-217.

Pennington et al., International Journal of Pharmaceutics, vol. 43 (1988), pp. 221-224.

Suzuki et al., Journal of Controlled Release, vol. 62 (1999), pp. 101-107.

Excerpts from the Handbook of Pharmaceutical Excipients (R.C. Rowe, P.J. Sheskey, & S.C. Owen, eds., PhP Pharmaceutical Press, 5th ed. 2006).

* cited by examiner

METHODS AND COMPOSITIONS FOR THE DELIVERY OF A THERAPEUTIC AGENT

RELATED APPLICATIONS

This application is a continuation of co-pending U.S. application Ser. No. 12/016,724, filed Jan. 18, 2008, which claims the benefit of and priority to Icelandic Patent Application Serial No. 8593/2007, filed Jan. 19, 2007, the entire disclosure of each of which is incorporated by reference herein for all purposes.

FIELD OF THE INVENTION

This invention relates generally to compositions for the delivery of a therapeutic agent and to related methods, and more particularly relates to compositions containing one or more alkoxy-polyethylene glycols for the delivery of a therapeutic agent and to related methods.

BACKGROUND

The administration of a therapeutic agent by injection (e.g., intravenous, intramuscular or subcutaneous injection) typically is regarded as the most convenient way of administration when the purpose is to achieve a rapid and strong systemic effect, for example, within 3-10 minutes, when the agent is not absorbed by the gastrointestinal tract, or when the agent is inactivated in the gastrointestinal tract or by first-pass hepatic metabolism. However, administration by injection presents a range of disadvantages. For example, sterile syringes must be used and injections cannot be administered by untrained personnel. Furthermore, this mode of administration may cause pain and/or irritation, especially in the case of repeated injections at the same site.

Mucosal administration, such as, intranasal, buccal, sublingual, rectal and pulmonal administration, is receiving particular interest as it avoids many of the disadvantages of injecting a therapeutic agent while, at the same time, still providing a strong and rapid systemic effect. In order to be an attractive alternative to injection, mucosal administration, for example, intranasal administration, should neither cause significant pain, discomfort or irritation nor cause any irreversible damage to the mucosal surface. However, in the case of acute health threatening indications, a relatively high local irritation to the mucosa may be acceptable.

In mucosal administration, such as during nasal, buccal or rectal administration, the therapeutic agent should be applied to the mucosa in a vehicle that permits it to penetrate, or be absorbed through, the mucosa. In order to penetrate the mucus, the vehicle should be biocompatible with mucus and hence have a certain degree of hydrophilicity. However, the vehicle should preferably also possess lipophilic properties to dissolve a clinically relevant amount of the therapeutic agent of interest.

The extensive network of blood capillaries under the mucosal surface, especially in the nasal mucosa, is well suited to provide a rapid and effective systemic absorption of drugs, vaccines and biologicals. Moreover, the nasal epithelial membrane in effect contains a single layer of epithelial cells (pseudostratified epithelium) and, therefore, is more suited for drug administration than other mucosal surfaces having squamous epithelial layers, such as, the mouth and vagina.

It has been hypothesized that the usefulness of nasal administration can be limited if the therapeutic agent has limited solubility in water (Proctor, D. F. (1985) *Nasal Physiology in Intranasal Drug Administrations*, in Chien, Y. W. (Ed.) TRANSNASAL SYSTEMIC MEDICATIONS, FUNDAMENTALS, DEVELOPMENTAL CONCEPTS AND BIOMEDICAL ASSESSMENTS, ELSEVIER Science Publishers, Amsterdam, pp. 101-105). As a result, this hypothesis, if correct, may limit the delivery of certain therapeutic agents that are sparingly soluble in water.

To facilitate delivery to the nasal cavity, an effective amount of the therapeutic agent should be dissolved in a small volume, for example, less than about 1000 µL, preferably less than 300 µL, and more preferably less than 150 µL. Larger volumes drain out anteriorly through the nostrils or posteriorly toward the pharynx where excess liquid is swallowed. As a result, if large volumes are administered, a portion of the therapeutic agent can be lost from the absorption site, and it can be difficult if not impossible to reproducibly administer the correct dose of the therapeutic agent.

A variety of delivery systems have been developed for the nasal administration of therapeutic agents. Lau and Slattery studied the absorption characteristics of diazepam and lorazepam following their intranasal administration for the treatment of epilepticus (Lau, S. W. J. & Slattery, J. T. (1989), *Absorption of Diazepam and Lorazepam Following Intranasal Administration*, INT. J. PHARM., 54, 171-174). In order to solubilize the therapeutic agent, a non-ionic surfactant—polyoxyethylated castor oil—was selected as the least irritating solvent of several solvents studied, including polyethylene glycol 400 (PEG 400). Diazepam absorption was 84% and 72%, respectively, in two adults measured over a period of 60 hours. However, the peak concentration was not observed until 1.4 hours after the nasal administration and was only about 27% with reference to intravenous administration, suggesting that most of the absorption had taken place after the test substance passed down to pharynx and swallowed. Similar results were obtained for lorazepam but with an even longer time to peak (2.3 hours). The authors concluded that the intranasal route of administration had limited potential for the acute treatment of epileptic seizures.

Wilton et al. attempted to administer midazolam to 45 children to achieve pre-anesthetic sedation (Wilton et al. (1988) *Preanaesthetic Sedation of Preschool Children Using Intranasal Midazolam*, ANESTHESIOLOGY, 69, 972-975). However, the volumes used were impractical and exceeded the maximal volume required for efficient administration. This resulted in coughing and sneezing with expulsion of at least part of the dose.

Morimoto et al. studied a gel preparation for nasal application in rats of nifedipine containing the gelling agent carbopol (polyacrylic acid) in PEG 400, for achieving prolonged action and high bioavailability of the therapeutic agent (Morimoto et al. (1987) *Nasal Absorption of Nifedipine from Gel Preparations in Rats*, CHEMICAL AND PHARMACEUTICAL BULLETINS, 35, No. 7, 3041-3044). A mixture of equal amounts of carbopol and PEG 400 was preferred. It was shown that nasal application provided higher bioavailability of nifedipine than after peroral administration, but the peak plasma concentration was not observed until 30 minutes after administration.

Danish Patent Application No. 2586/87 discloses a pharmaceutical composition comprising an anti-inflammatory steroid, water, 2 to 10% (v/v) propylene glycol, 10 to 25% (v/v) PEG 400, and 1 to 4% (v/v) Tween 20.

U.S. Pat. No. 4,153,689 discloses a stable aqueous solution of insulin intended for intranasal administration. The solutions had a pH not more than 4.7, and contained from 0.1 to 20% by weight of a stabilizing agent including (a) one or more non-ionic surface active agents whose hydrophile-lipophile balance value was in the range of 9 to 22, and/or (b) polyethylene glycol whose molecular weight was in the range of from 200 to 7500. Exemplary non-ionic surface active agents included polyoxyethylene fatty acid ester, a polyoxyethylene higher alcohol ether, a polyoxyethylene alkylphenyl ether, or a polyoxyethylene alkylphenyl ether, or a polyoxyethylene hydrogenated castor oil.

International Patent Publication No. DK-2075/90 discloses the nasal administration of therapeutic agents, for example, benzodiazepines, in compositions containing n-glycofurol, a derivative of polyethyleneglycol, for mucosal administration. The application discloses the nasal administration of therapeutic agents, for example, benzodiazepines, in formulations containing at least 30% n-ethyleneglycols ranging from 1-8 ethylene glycol, for example, polyethylene glycol 200 (PEG 200).

U.S. Pat. No. 5,693,608 discloses a method of administering a therapeutic agent via the nasal mucosa of a mammal, where the agent is dissolved or suspended in an n-ethyleneglycol containing vehicle where the n-ethyleneglycol is represented by the formula, $H(OCH_2CH_2)_pOH$, wherein p is a number from 1 to 8.

Notwithstanding, there is still a need for compositions deliverable through mucosal membranes that produce therapeutic plasma concentrations of the therapeutic agent as fast as or nearly as fast as by intravenous administration but without causing irritation and/or unacceptable damage to the mucosal membrane.

SUMMARY OF THE INVENTION

The invention is based, in part, upon the discovery that the inclusion of one or more alkoxy-polyethylene glycols in a formulation provides certain advantages when the resulting composition is to be applied, for example, to a mucosal surface. For example, it has been discovered that when alkoxy-polyethylene glycol is used in such formulations, the therapeutic agent can be still be solubilized (which is especially useful for poorly soluble therapeutic agents) but the resulting formulations are less viscous and cause less irritation to mucosal membranes because the amount of other potentially viscous and irritable excipients, for example, polyethylene glycol or propylene glucol, can be reduced or eliminated altogether. As a result, the lower viscosity formulations, when converted into droplets, for example, by a nasal sprayer during intranasal delivery, can produce a spray pattern optimized for delivering the therapeutic agent to the mucosal membrane. In addition, formulations containing alkoxy-polyethylene glycols create less irritation (burning sensation) when applied to a mucosal surface, for example, a nasal membrane following nasal administration. In addition, when administered intranasally, the compositions of the invention minimize undesirable after taste (for example, a petroleum-like after taste) that can be associated with certain other excipients.

In one aspect, the invention provides a liquid pharmaceutical composition comprising a therapeutic agent and an alkoxy-polyethylene glycol represented by Formula I:

$$R\!-\!O\!-\!(CH_2CH_2O)_n\!-\!H \quad (I)$$

wherein,

R is methyl, ethyl, n-propyl, isopropyl, or cyclopropyl; and n, which is the average number of oxyethylene repeating units, is a number in the range of from about 1 to about 25.

In another aspect, the invention provides a liquid formulation for solubilizing a poorly soluble therapeutic agent, for example, a poorly soluble organic therapeutic agent. The composition comprises a poorly soluble therapeutic agent and an alkoxy-polyethylene glycol represented by Formula I:

$$R\!-\!O\!-\!(CH_2CH_2O)_n\!-\!H \quad (I)$$

wherein,

R is $(C_1\text{-}C_6)$alkyl; and n, which is the average number of oxyethylene repeating units, is a number in the range of from about 1 to about 25.

In another aspect, the invention provides methods of delivering a therapeutic agent of interest to a mammal, for example, a human, using an alkoxy-polyethylene glycol containing composition described herein. The composition is particularly useful when the composition is applied to a mucosal membrane, for example, a nasal membrane during intranasal drug delivery.

These and other aspects and advantages of the invention will become apparent upon consideration of the following detailed description and claims.

DETAILED DESCRIPTION OF THE INVENTION

The invention is based, in part, upon the discovery that the inclusion of one or more alkoxy-polyethylene glycols into formulations provides certain advantages over other excipients when the formulations are applied, for example, to a mucosal surface. For example, it has been discovered that when an alkoxy-polyethylene glycol is used in such a formulation, the therapeutic agent (for example, a poorly soluble therapeutic agent) can be solubilized more easily and in larger amounts than when other excipients, for example, polyethylene glycol (more particularly PEG 400), are used. However, the resulting formulations are less viscous and cause less irritation to mucosal membranes as the amount of other viscous and irritable excipients can be reduced or eliminated altogether. As a result, the lower viscosity formulations, when converted into droplets, for example, by a nasal sprayer during intranasal delivery, produce a spray pattern optimized for delivering the therapeutic agent to the mucosal membrane. In addition, formulations containing one or more alkoxy-polyethylene glycols cause less irritation (for example, a burning sensation) when applied to a mucosal surface, for example, a nasal membrane during intranasal administration. In addition, when administered intranasally, the compositions of the invention have less undesirable after taste (for example, a petroleum-like after taste) than when other excipients, for example, propylene glycol, are used.

Under certain circumstances, the alkoxy-group also increases the bioadhesion of the composition to the site of administration on the mucosal surface thereby prolonging the duration of the composition at the site of administration. This can increase the amount of therapeutic agent that is ultimately absorbed.

I—Formulations

In one aspect, the invention provides a liquid pharmaceutical composition comprising a therapeutic agent and an alkoxy-polyethylene glycol represented by Formula I:

$$R\!-\!O\!-\!(CH_2CH_2O)_n\!-\!H \quad (I)$$

wherein,

R is methyl, ethyl, n-propyl, isopropyl, or cyclopropyl; and n is the average number of oxyethylene repeating units and is a number in the range of from about 1 to about 25.

In another aspect, the invention provides a liquid formulation for solubilizing a poorly soluble therapeutic agent. The liquid pharmaceutical composition comprises a poorly soluble therapeutic agent, for example, a poorly soluble organic therapeutic agent, and an alkoxy-polyethylene glycol represented by Formula I:

$$R\!-\!O\!-\!(CH_2CH_2O)_n\!-\!H \quad (I)$$

wherein,

R is (C$_1$-C$_6$)alkyl; and n is the average number of oxyethylene repeating units and is a number in the range of from about 1 to about 25. The formulations typically are in liquid form at 20° C., 25° C., 30° C., 35° C., or 40° C. Certain formulations preferably are liquid formulations at 37° C.

The term "poorly soluble therapeutic agent" refers to a compound having biological activity and a solubility in water of less than about 1 mg/mL at pH 7 and 20° C. In certain embodiments, the poorly soluble therapeutic agent is an organic compound that has a molecular weight of less than 1500 g/mol, and preferably less than 500 g/mol. In certain embodiments, the poorly soluble therapeutic agent is a compound, for example, an organic compound, having an aqueous solubility of less than about 0.5 mg/mL, less than about 0.3 mg/mL, or less than about 0.1 mg/mL, at pH 7 and 20° C.

In addition, the term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term "(C$_1$-C$_6$)alkyl" refers to an alkyl group having between 1 and 6 carbon atoms. Representative alkyl groups include methyl, ethyl, n-propyl, isopropyl, n-butyl, sec-butyl, isobutyl, tert-butyl, pentyl, hexyl, cyclopropyl, cyclobutyl, cyclopropylmethylene, cyclopentyl, cyclobutylmethylene, cyclobutylethylene, cyclohexyl, cyclopropylpropylene, cyclobutylethylene, and cyclopentylmethylene. The term cyclopropylmethylene, for example, is art-recognized and refers to a radical having the following formula:

In certain embodiments, the alkoxy-polyethylene glycol can comprise from about 0.1% (v/v) to about 80% (v/v), or from about 0.5% (v/v) to about 70% (v/v), of the composition. In certain other embodiments, the alkoxy-polyethylene glycol can comprise from about 5% (v/v) to about 80% (v/v), or from about 30% (v/v) to about 75% (v/v) or from about 40% (v/v) to about 70% (v/v), of the composition. For certain hydrophilic drugs, the alkoxy-polyethylene glycol can comprise from about 0.1% (v/v) to about 80% (v/v), or from about 0.5% (v/v) to about 70% (v/v), or from about 1% (v/v) to about 60% of the composition. For certain lipophilic drugs, the alkoxy-polyethylene glycol can comprise from about 1% (v/v) to about 80% (v/v), or from about 2% (v/v) to about 65% (v/v), or from about 5% (v/v) to about 50% of the composition. Furthermore, the therapeutic agent can comprise from about 0.001% (w/v) to about 20% (w/v) of the composition, or from about 0.1% (w/v) to about 10% (w/v) of the composition.

The pharmaceutical composition can have a pH in the range of from about 4.5 to about 8.5, or from about 4.5 to about 7.5, or from about 4.5 to about 6.5, or from about 5.5 to about 8.5, or from about 6.5 to about 8.5, or from about 5.5 to about 7.5.

As discussed, one of the advantages of using an alkoxy-polyethylene glycol is that it can be used in place of or can be used to reduce the amount of other excipients, for example, certain polyethylene glycols and propylrnr glycol, so as to reduce the viscosity of the resulting formulation. By reducing the viscosity of the resulting formation it is possible to create sprays that have more uniform spray characteristics (for example, more uniform droplet sizes and/or plume geometries) for the intranasal administration of therapeutic agent. The resulting pharmaceutical composition at a temperature of 20° C. has a viscosity in the range of about 1.5 cP to about 60 cP, or from about 2 cP to about 50 cP, or from about 3 cP to about 40 cP, or from about 4 cP to about 30 cP, or from about 5 cP to about 25 cP.

Exemplary alkoxy-polyethylene glycols, therapeutic agents, and other excipients useful in creating compositions of the invention are described in the following sections.

A. Alkoxy-Polyethylene Glycol

Useful alkoxy-polyethylene glycol excipients useful in the practice of the invention are represented by Formula (I):

$$R—O—(CH_2CH_2O)_n—H \quad (I)$$

wherein, n, as the average number of oxyethylene repeating units, is a number in the range of from about 1 to about 25. Accordingly, n can be a number about 1, 2, 3, 4, 5, 6, 7, 8, 9, 10, 11, 12, 13, 14, 15, 16, 17, 18, 19, 20, 21, 22, 23, 24, or 25. In certain embodiments, n is an number in the range of from about 2 to about 15, or from about 2 to about 14, or from about 2 to about 13, or from about 2 to about 12, or from about 2 to about 11, or from about 2 to about 10, or from about 3 to about 15, or from about 3 to about 14, or from about 3 to about 13, or from about 3 to about 12, or from about 3 to about 11, or from about 3 to about 10.

In certain embodiments, R is $(C_1-C_6)$alkyl. For example, as discussed above, R can be methyl, ethyl, n-propyl, isopropyl, n-butyl, sec-butyl, isobutyl, tert-butyl, pentyl, hexyl, cyclopropyl, cyclobutyl, cyclopropylmethylene, cyclopentyl, cyclobutylmethylene, cyclobutylethylene, cyclohexyl, cyclopropylpropylene, cyclobutylethylene, or cyclopentylmethylene. In certain embodiments, R is selected from the group consisting of methyl, ethyl, n-propyl, isopropyl, and cyclopropyl.

In a preferred embodiment, the alkoxy-polyethylene glycol is methoxy-polyethylene glycol where R is methyl and n is an number from about 1 to about 25, or from about 2 to about 12, or from about 3 to about 10.

Useful methoxy-polyethylene glycols include, for example, methoxy-diethyleneglycol (m2EG), methoxy-triethylene glycol (m3EG), methoxy-tetraethylene glycol (m4EG), methoxy-pentaethylene glycol (m5EG), methoxy-hexaethylene glycol (m6EG), methoxy-heptaethylene glycol (m7EG), methoxy-octaethylene glycol (m8EG), methoxy-nonaethylene glycol (m9EG), methoxy-decaethylene glycol (m10EG), methoxy-undecaethylene glycol (m11EG), methoxy-dodecaethylene glycol (m12EG), methoxy-tridecaethylene glycol (m13EG) and methoxy-tetradecaethylene glycol (m14EG). The ethylene glycols may be used in the form of the single compounds or as a mixture of two or more methoxy-n-ethylene glycols.

In certain embodiments, the alkoxy-polyethylene glycol is methoxy-polyethylene glycol 350 (mPEG 350) or is methoxy-polyethylene glycol 550 (mPEG 550) or is methoxy-polyethylene glycol 750 (mPEG 750). The term "mPEG 350" is understood to mean methoxy polyethylene glycol having an average molecular weight of about 350, and in certain embodiments "n," as denoted in Formula I, is 7.2. The term "mPEG550" is understood to mean methoxy polyethylene glycol having an average molecular weight of about 550, and in certain embodiments "n," as denoted in Formula I, is 11.8. The term "mPEG750" is understood to mean methoxy polyethylene glycol having an average molecular weight of about 750, and in certain embodiments "n," as denoted in Formula I, is 16.3.

Certain, preferred alkoxy-polyethylene glycols include Carbowax™ mPEG 350, Carbowax™ mPEG 550 or Carbowax™ mPEG 750, which are available commercially from Dow Chemical Company. Both mPEG350 and mPEG550 are colorless liquids that are miscible with water, alcohols, such as methanol, ethanol, n-propanol, glycerol and various oils in all proportions, and have a boiling point about 155° C. It is understood that alkoxy-polyethylene glycols are known by other names, where, for example, methoxy-polyethylene glycol is also known as mono-methyl polyethylene glycol and poly(ethylene glycol) methyl ether.

By using one or more of the alkoxy-polyethylene glycols described herein, the resulting pharmaceutical compositions can be optimized, for example, with respect to bioadhesion, viscosity and sprayability. For example, mPEG 350, at an equivalent concentration as PEG 200, can still solubilize a therapeutic agent but the resulting composition has a lower viscosity. As a result, this substitution has a surprisingly positive effect on the sprayability compared with lower molecular weight PEG 200, which is important where the formulation is to be sprayed.

B. Therapeutic Agent

The pharmaceutical composition of the invention may comprise one or more therapeutic agents (also referred to as biologically active substances) selected from the group consisting of hydrophobic therapeutic agents, hydrophilic therapeutic agents, and combinations thereof.

The alkoxy-polyethylene glycol excipients are surprisingly capable of solubilizing and delivering a wide variety of hydrophilic and hydrophobic therapeutic agents. The hydrophobic drugs have little or no water solubility. It is understood that the excipients described herein can be used to solubilize therapeutic agents that have a solubility in water of less than about 1.0 mg/mL, less than about 0.5 mg/mL, less than about 0.3 mg/mL, or less than about 0.1 mg/mL, or less than about 0.01 mg/mL, at pH 7 and 20° C. Such therapeutic agents can be any agents having therapeutic or other value when administered to a mammal, for example, a human, and can include organic molecules (for example, small molecule drugs having a molecular weight of less than 1,500 g/mol., or less than 500 g/mol.), proteins, peptides, immungens (e.g. vaccines, cytokines, etc.), nutrients, and cosmetics (cosmeceuticals).

In certain embodiments, the therapeutic agent is an analgesic agent, an anti-inflammatory agent, an anti-arrhythmic agent, an anti-asthma agent, an anti-bacterial agent, an anti-viral agent, an anti-coagulant, an anti-depressant, an anti-diabetic, an anti-epileptic, an anti-fungal agent, an anti-hypertensive agent, an anti-malarial, an anti-migraine agent, an anti-muscarinic agent, an anti-neoplastic agent, an immunosuppressant, an anti-protozoal agent, an anti-thyroid agent, an anxiolytic agent, a sedative, a hypnotic agent, a neuroleptic agent, a beta-Blocker, a cardiac inotropic agent, a corticosteroid, a diuretic agent, an anti-Parkinsonian agent, a gastrointestinal agent, an anti-histamine, a histamine-receptor antagonist, a lipid regulating agent, a muscle relaxant, nitrate and other anti-anginal agent, a nutritional agent, an opioid analgesic, sex hormone, stimulant, cytokine, peptidomimetic, peptide, protein, toxoid, sera, antibody, vaccine, nucleoside, nucleotide, nucleic acid and peptidyl-nucleic acid.

Specific non-limiting examples of hydrophobic therapeutic agents that can be used in the pharmaceutical compositions of the present invention include the following representative compounds, as well as their pharmaceutically acceptable salts, isomers, esters, ethers and other derivatives including, for example: (1) analgesics and anti-inflammatory agents, such as, aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, oxaprozin, oxyphenbutazone, phenylbutazone, piroxicam, refocoxib, sulindac, tetrahydrocannabinol, tramadol and tromethamine; (2) anti-arrhythmic agents, such as, amiodarone HCl, diisopyramide, flecaimide acetate and quinidine sulfate; (3) anti-asthma agents, such as, zileuton, zafirlukast, montelukast, and albuterol; (4) anti-bacterial agents, such as, baclofen, benzathine penicillin, cinoxacin, clarithromycin, clofazimine, cloxacillin, demeclocycline, dirithromycin, doxycycline, erythromycin, ethionamide, furazolidone, grepafloxacin, imipenem, levofloxacin, lomefloxacin, moxifloxacin HCl, nalidixic acid, nitrofurantoin, norfloxacin, ofloxacin, rifampicin, rifabutin, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim and trovafloxacin; (5) anti-viral agents, such as, abacavir, amprenavir, delavirdine, efavirenz, indinavir, lamivudine, nelfinavir, nevirapine, ritonavir, saquinavir, and stavudine; (6) anti-coagulants, such as, cilostazol, clopidogrel, dicumarol, dipyridamole, nicoumalone, oprelvekin, phenindione, ticlopidine, and tirofiban; (7) anti-depressants, such as amoxapine, bupropion, citalopram, clomipramine, maprotiline HCl, mianserin HCl, nortriptyline HCl, paroxetine HCl, sertraline HCl, trazodone HCl, trimipramine maleate, and venlafaxine HCl; (8) anti-diabetics, such as, acetohexamide, chlorpropamide, glibenclamide, gliclazide, glipizide, glimepiride, miglitol, pioglitazone, repaglinide, rosiglitazone, tolazamide, tolbutamide and troglitazone; (9) anti-epileptics, such as, beclamide, carbamazepine, clonazepam, ethotoin, felbamate, fosphenyloin sodium, lamotrigine, methoin, methsuximide, methylphenobarbitone, oxcarbazepine, paramethadione, phenacemide, phenobarbitone, phenyloin, phensuximide, primidone, sulthiame, tiagabine HCl, topiramate, valproic acid, and vigabatrin; (10) anti-fungal agents, such as, amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine HCl, terconazole, tioconazole and undecenoic acid; (11) anti-hypertensive agents, such as, amlodipine, benidipine, benezepril, candesartan, captopril, darodipine, diltiazem HCl, diazoxide, doxazosin HCl, elanapril, eprosartan, losartan mesylate, felodipine, fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, and valsartan; (12) anti-malarials, such as, amodiaquine, chloroquine, chlorproguanil HCl, halofantrine HCl, mefloquine HCl, proguanil HCl, pyrimethamine and quinine sulfate; (13) anti-migraine agents, such as, dihydroergotamine mesylate, ergotamine tartrate, frovatriptan, methysergide maleate, naratriptan HCl, pizotyline malate, rizatriptan benzoate, sumatriptan succinate, and zolmitriptan; (14) anti-muscarinic agents, such as, atropine, benzhexyl HCl, biperiden, ethopropazine HCl, hyoscyamine, oxyphencyclimine HCl and tropicamide; (15) anti-neoplastic agents and immunosuppressants, such as, aminoglutethimide, amsacrine, azathioprine, bicalutamide, bisantrene, busulfan, camptothecin, chlorambucil, cyclosporin, dacarbazine, ellipticine, estramustine, etoposide, irinotecan, lomustine, melphalan, mercaptopurine, mitomycin, mitotane, mitoxantrone, mofetil mycophenolate, nilutamide, paclitaxel, procarbazine HCl, sirolimus, tacrolimus, tamoxifen citrate, teniposide, testolactone, topotecan HCl, and toremifene citrate; (16) antiprotozoal agents, such as, atovaquone, benznidazole, clioquinol, decoquinate, diiodohydroxyquinoline, diloxanide furoate, dinitolmide, furazolidone, metronidazole, nimorazole, nitrofurazone, omidazole and tinidazole; (17) anti-thyroid agents, such as, carbimazole, paracalcitol, and propylthiouracil; anti-tussives, such as, benzonatate; (18) anxiolytics, sedatives, hypnotics and neuroleptics, such as, alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, fluanisone, flunitrazepam, triflupromazine, flupenthixol decanoate, fluphenazine decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, proclorperazine, pseudoephedrine, quetiapine, rispiridone, sertindole, sulpiride, temazepam, thioridazine, triazolam, zolpidem, and zopiclone; (19) beta-Blockers, such as, acebutolol, alprenolol, labetalol, metoprolol, nadolol, oxprenolol, pindolol and propranolol; (20) cardiac inotropic agents, such as, aminone, digitoxin, digoxin, enoximone, lanatoside C and medigoxin; (21) a corticosteroid, such as, beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone; (22) diuretics, such as, acetazolamide, amiloride, bendroflumethiazide, bumetamide, chlorothiazide, chlorthalidone, ethacrynic acid, frusemide, metolazone, spironolactone and triamterene; (23) anti-Parkinsonian agents, such as, bromocriptine mesylate, lysuride maleate, pramipexole, ropinirole HCl, and tolcapone; (24) gastrointestinal agents, such as bisacodyl, cimetidine, cisapride, diphenoxylate HCl, domperidone, famotidine, lansoprazole, loperamide, mesalazine, nizatidine, omeprazole, ondansetron HCl, rabeprazole sodium, ranitidine HCl and sulphasalazine; (25) anti-histamines and histamine-receptor antagonists, such as, acrivastine, astemizole, chlorpheniramine, cinnarizine, cetirizine, clemastine fumarate, cyclizine, cyproheptadine HCl, dexchlorpheniramine, dimenhydrinate, fexofenadine, flunarizine HCl, loratadine, meclizine HCl, oxatomide, and terfenadine; (26) lipid regulating agents, such as, atorvastatin, bezafibrate, cerivastatin, ciprofibrate, clofibrate, fenofibrate, fluvastatin, gemfibrozil, pravastatin, probucol, and simvastatin; (27) muscle relaxants, such as, dantrolene sodium and tizanidine HCl; (28) nitrates and other anti-anginal agents, such as, amyl nitrate, glyceryl trinitrate, isosorbide dinitrate, isosorbide mononitrate and pentaerythritol tetranitrate; (29) nutritional agents, such as, calcitriol, carotenes, dihydrotachysterol, essential fatty acids, non-essential fatty acids, phytonadiol, vitamin A, vitamin $B_2$, vitamin D, vitamin E and vitamin K; (30) opioid analgesics, such as, codeine, dextropropoxyphene, diamorphine, dihydrocodeine, fentanyl, meptazinol, methadone, morphine, hydromorphone, nalbuphine and pentazocine; (31) sex hormones, such as, clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone and tibolone; and (32) stimulants, such as, amphetamine, dexamphetamine, dexfenfluramine, fenfluramine and mazindol; and others, such as, becaplermin, donepezil HCl, L-thryroxine, methoxsalen, verteporfin, physostigmine, pyridostigmine, raloxifene HCl, sibutramine HCl, sildenafil citrate, tacrine, tamsulosin HCl, and tolterodine.

Certain exemplary hydrophobic therapeutic agents include sildenafil citrate, amlodipine, tramadol, celecoxib, rofecoxib, oxaprozin, nabumetone, ibuprofen, terbinafine, itraconazole, zileuton, zafirlukast, cisapride, fenofibrate, tizanidine, nizatidine, fexofenadine, loratadine, famotidine, paricalcitol, atovaquone, nabumetone, alprazolam, bromazepam, chlorpromazine, clonazepam, diazepam, flunitrazepam, flurazepam, haloperidol, lorazepam, lormetazepam, midazolam, nitrazepam, oxazepam, pseudoephedrine, temazepam, triazolam, zolpidem, zopiclone, tetrahydrocannabinol, testosterone, megestrol acetate, repaglinide, progesterone, rimexolone, cyclosporin, tacrolimus, sirolimus, teniposide, paclitaxel, pseudoephedrine, troglitazone, rosiglitazone, finasteride, vitamin A, vitamin D, vitamin E, and pharmaceutically acceptable salts, isomers and derivatives thereof. It should be appreciated that the listing of hydrophobic therapeutic agents and their therapeutic classes is merely illustrative. It is understood, that mixtures of hydrophobic therapeutic agents may also be used where desired.

An advantage of using alkoxy-polyethylene glycol as an excipient in the pharmaceutical composition is that, for example, highly lipophilic substances, such as, lorazepam, midazolam, clonazepam, alprazolam and other compounds belonging to the benzodiazepines, as well as water soluble substances, for example, peptides and proteins, such as, the pancreatic hormones can be solubilized in a clinically relevant volume (for example, 25-300 μL) for delivery to a human subject. By way of comparison, clinically relevant doses of midazolam, lorazepam, alprazolam, diazepam and clonazepam would have to be dissolved in at least 5 mL of water.

Although the alkoxy-polyethylene glycol excipients are particularly useful for the delivery of hydrophobic agents, alkoxy-polyethylene glycol can also be used to deliver a variety of hydrophilic therapeutic agents. Alkoxy-polyethylene glycols, under certain circumstances, may prolong the duration of the therapeutic agent at the absorption site thereby increasing the amount of agent ultimately delivered. Exemplary hydrophilic therapeutic agents include hydrophilic drugs (i.e., conventional non-peptidic drugs), hydrophilic macromolecules, such as, cytokines, peptides, proteins, peptidomimetics, toxoids, sera, antibodies, vaccines, nucleosides, nucleotides, nucleic acids, and genetic material. The hydrophilic therapeutic agent can be administered alone or in combination with other agents, for example, a hydrophobic therapeutic agent discussed hereinabove or a second, different hydrophilic therapeutic agent.

Without limitation, exemplary hydrophilic therapeutic agents that can be delivered using the compositions and methods of the present invention, include the following compounds as well as their pharmaceutically acceptable salts, isomers, esters, ethers and other derivatives, for example: acarbose; acyclovir; acetyl cysteine; acetylcholine chloride; alatrofloxacin; alendronate; alglucerase; amantadine hydrochloride; ambenomium; amifostine; aminocaproic acid; antihemophilic factor (human); antihemophilic factor (porcine); antihemophilic factor (recombinant); aprotinin; asparaginase; atenolol; atracurium besylate; azithromycin; aztreonam; BCG vaccine; bacitracin; becalermin; belladonna; bepridil hydrochloride; bleomycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotaxime; cefoxitin sodium; ceftizoxime; ceftriaxone; cefuroxime axetil; cephalexin; cephapirin sodium; cholera vaccine; chorionic gonadotropin; cidofovir; cisplatin; cladribine; clidinium bromide; clindamycin and clindamycin derivatives; ciprofloxacin; clondronate; colistimethate sodium; colistin sulfate; corticotropin; cosyntropin; cromalyn sodium; cytarabine; daltaperin sodium; danaproid; deforoxamine; denileukin diftitox; desmopressin; diatrizoate megluamine and diatrizoate sodium; dicyclomine; didanosine; dopamine hydrochloride; dornase alpha; doxacurium chloride; doxorubicin; editronate disodium; elanaprilat; enkephalin; enoxacin; enoxaparin sodium; ephedrine; epinephrine; epoetin alpha; esmol hydrochloride; Factor IX; famiciclovir; fludarabine; fluoxetine; foscarnet sodium; ganciclovir; granulocyte colony stimulating factor; granulocyte-macrophage stimulating factor; growth hormones (human or bovine); gentamycin; glucagon; glycopyrrolate; gonadotropin releasing hormone and synthetic analogs thereof; GnRH; gonadorelin; grepafloxacin; hemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin-porcine; insulin NPH; insulin aspart; insulin glargine; insulin detemir; interferon-$\alpha$; interferon-$\beta$; ipratropium bromide; isofosfamide; japanese encephalitis virus vaccine; leucovorin calcium; leuprolide acetate; levofloxacin; lincomycin and lincomycin derivatives; lobucavir; lomefloxacin; loracarbef; mannitol; measles virus vaccine; meningococcal vaccine; menotropins; mephenzolate bromide; mesalmine; methanamine; methotrexate; methscopolamine; metformin hydrochloride; metoprolol; mezocillin sodium; mivacurium chloride; mumps viral vaccine; nedocromil sodium; neostigmine bromide; neostigmine methyl sulfate; neutontin; norfloxacin; octreotide acetate; olpadronate; oxytocin; pamidronate disodium; pancuronium bromide; paroxetine; pefloxacin; pentamidine isethionate; pentostatin; pentoxifylline; periciclovir; pentagastrin; phentolamine mesylate; phenylalanine; physostigmine salicylate; plague vaccine; piperacillin sodium; platelet derived growth factor-human; pneumococcal vaccine polyvalent; poliovirus vaccine (live or inactivated); polymixin B sulfate; pralidoxime chloride; pramlintide; pregabalin; propafenone; propenthaline bromide; pyridostigmine bromide; rabies vaccine; residronate; ribavarin; rimantadine hydrochloride; rotavirus vaccine; salmetrol xinofoate; sincalide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valaciclovir; varicella virus vaccine live; vasopressin and vasopressin derivatives; vecoronium bromide; vinblastin; vincristine; vinorelbine; warfarin-sodium; yellow fever vaccine; zalcitabine; zanamavir; zolandtronate; and zidovudine.

Other therapeutic agents that can be administered in this formulation may comprise adrenal hormones, corticosteroids and derivatives, such as, ACTH and analogs thereof, tetracosactrin, alsactide, cortisone, hydrocortisone alcohol, hydrocortisone acetate, hydrocortisone hemisuccinate, prednisolone terbutate, 9-alpha-fluoroprednisolone, triamcinolone acetonide, dexamethasone phosphate, flunisolide, toxicorol pivalate; anorectics, such as, benzphetamine HCl chlorphentermine HCl; antibiotics, such as, tetracycline HCl, tyrothricin, cephalosporine, aminoglycosides, streptomycin, gentamycin, leucomycin, penicillin and derivatives; anti-allergic agents; antibodies, such as, monoclonal or polyclonal antibodies; anti-cholinergic agents; anti-depressants, such as, amitriptyline HCl, imipramine HCl; anti-emitics, such as, neuroleptica, for example, metopimazin, anti-emetics having a regulatory effect on the motility of the intestine, such as, domperidon; anti-histaminic agents and histaminic agents, such as, diphenhydramin HCl, chloropheniramine maleate, histamine, prophenpyridamine maleate, chlorprophenyridamine maleate, disodium chromoglycate, meclizine; anti-hypertensive agents, such as, clonidine HCl; anti-inflammatory agents (enzymatic), such as, chymotrypsin, bromelain seratiopeptidase; anti-inflammatory agents (non-steroidal), such as, acetaminophen, aspirin, aminopyrine, phenylbutazone, colchicine, probenocid; anti-inflammatory agents (steroidal), such as, fluticasone, predonisolone, triaxncinolone acetonide; anti-neoplastic agents, such as, actinomycin C.; anti-septics, such as, chlorhexidine HCl, hexylresorcinol, dequalinium chloride, ethacridine; anti-tussive expectorant (asthmatic agents), such as, sodium chromoglycate, isoproterenol HCl; anti-viral and anti-cancer agents such as interferons (such as alpha-2 interferon for treatment of common colds), phenyl-p-guanidino benzoate, enviroxime, etc.; beta-adrenergic blocking agents, such as, propranolol HCl; blood factors, such as, factor VII, factor VIII; bone metabolism controlling agents, such as, vitamin $D_3$; bronchoisters, such as, clenbuterol HCl, bitolterol mesylate; cardiotonics such as digitalis; cardiovascular regulatory hormones, drugs and derivatives, such as, bradykin antagonists, atrial natriuretic peptide and derivatives, such as, hydrailsazine, angiotensin II antagonist, nitroglycerin, propranolol, clofilium rosylate; chemotherapeutic agents, such as, sulphathiazole, nitrofurazone; CNS-stimulants, such as, lidocaine, cocaine; corticosteroids, such as, lacicortone, hydrocortisone, fluocinolone acetonide, triamcinolone acetonide; enzymes, such as, lysozyme chloride, dextranase; gastrointestinal hormones and derivatives, such as, secretin, substance P; hypothalamus hormones and derivatives, such as, LHRH and analogues (such as naferelin, buserelin, zolidex), TRH (thyrotropin releasing hormone); hypotensives; local anaesthetics, such as, benzocaine; migraine treatment substances, such as, dihydroergot amine, ergometrine, ergotamine, pizotizin; pancreatic hormones and derivatives, such as, insulin (hexameric/dimeric/monomeric forms); parasympathomimetics, such as, nicotine, methacholine; parasympatholytics, such as, scopolamine, atropine, ipratropium; Parkinson's disease substances, such as, apomorphin; pituitary gland hormones and derivatives, such as, growth hormone (e.g. human), vasopressin and analogues (DDAVP, Lypressin); prostaglandins, such as, PGA and derivatives thereof, $PGE_1$ and derivatives thereof, $PGE_2$ and derivatives thereof, $PGF_1$ and derivatives thereof, dinoprost trometamol; protease inhibitors, such as, citrate, or $\alpha_1$-antitrypsin; sex-hormones, such as, ethinyloestradiol, levonorgestrel, FSH, LH, LTH, estradiol-17-beta, norethindrone; sympathomimetics, such as, phenylephrine, xylometazoline, tramazoline, dopamine, dobutamine; sleep-aids, such as granisetron and rameltean, tranquilizers, such as, brotizolam, camazepam, chlorazepic acid, cloxazolam, delorazepam, estazolam, ethyl loflazepate, fludiazepam, flutazolam, halazepam, haloxazolam, ketazolam, laprazolam, lormetazepam, nimetazepam, nitrazepam, nordiazepam, oxazepam, pinazepam, prazepam, temazepam, tetrazepam, tofisopam; vaccines, such as, AIDS-vaccines, parainfluenza virus, polio, rhinovirus type 13, respiratory syncytial virus; vasoconstrictors, such as, phenylephrine HCl, tetrahydrozoline HCl, naphazoline nitrate, oxymetazoline HCl, tramazoline HCl; vasodilators, such as, papaverine HCl, Substance P, vasoactive intestinal peptide (VIP).

Certain exemplary formulations comprising alkoxy-polyethylene glycol also comprise one or more therapeutic agents selected from the group consisting of peptide drugs, such as, oxytocin, vasopressin (desmopressin), insulin, calcitonin, elcatonin, cyanocobalamin $B_{12}$, and glucagon-like protein-1 (GLP-1), and small organic molecules, such as, dinoprsoone, misoprostol, apomorphine, fentanyl, metoclopramide, butorphanol, and midazolam C. Other Excipients It is understood that the compositions of the invention, in addition to the alkoxy-polyethylene glycol and the therapeutic agent, can comprise a number of other excipients known to those skilled in the art, including absorption promoters, buffering agents, water absorbing polymers, alcohols, lipids, osmotic pressure controlling agents, pH-controlling agents, preservatives, propellants, surfactants, enzyme inhibitors, excipients for adjusting hydrophilic-lipophilic balance (HLB) and stabilizers.

Exemplary surfactants, include, for example nonoxynol, octoxynol, tweens, spans, sodium lauryl sulfate, and sorbitan monopalmitate. Exemplary absorption promoters include, for example, bile salts and derivatives thereof, fusidic acid and derivatives thereof, oleic acid, lecithin, lysolechitins, dodecanoyl phosphatidylcholine (DDPC), sucrose mon-odododecanoate, n-dodecyl-β-D-maltopyranoside, pectin, chitosan, α-, β- and γ-cyclodextrins and derivatives thereof, pegylated caprylic-/capric glycerides and derivatives thereof, such as, Softigen and Labrasol. Exemplary water absorbing polymers include, for example, polyethylene glycols having an average molecular weight ranging from 200 to 7500, propylene glycol, or mixtures thereof, or single ethylene glycols such as tetraethylene glycol and pentaethylene glycol. Exemplary alcohols include, for example, ethanol, isopropyl alcohol. Exemplary lipids include, for example, vegetable oil, soybean oil, peanut oil, coconut oil, maize oil, olive oil, sunflower oil, monoglycerides, diglycerides, mono/diglycerides, mono/di/triglycerides. Exemplary osmotic pressure controlling agents include, for example, glycerol, dextrose, maltose, sucrose, mannitol, xylitol, various salts (for example, sodium chloride). Exemplary pH-controlling agents include, for example, buffers, acids (for example, nitric acid, phosphoric acid, or acetic acid). Exemplary preservatives include, for example, methyl paraoxybenzoate, phenyl ethyl alcohol or benzoic acid. Exemplary propellants, include, for example, butane or air displacement such as nitrogen. Excipients adjusting the HLB of the formulation include, for example, Tween 20, 25, 40, 45, 65, 85, Span 20-80, Brij 30-98, acacia. Exemplary enzyme inhibitors include, for example aprotinin and other peptidase inhibitors, diisopropylfluorophosphate (DFP), carbopol. Exemplary stabilizers include, for example, cyclodextrins.

Although it is understood that the alkoxy-polyethylene glycols described herein, for example, methoxy-polyethylene glycol, can solubilize poorly soluble therapeutic agents, under certain circumstances, it may be helpful to include additional compounds that enhance the solubility of the therapeutic agent. Examples of such solubilizers include, for example, alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, pegylated-mono/di-caprylic/capric glycerides, polyvinylalcohol, hydroxypropyl methylcellulose and other cellulose derivatives, cyclodextrins (for example, α-, β-, or γ-cyclodextrins) and cyclodextrin derivatives; ethers of polyethylene glycols having an average molecular weight of about 200 to about 6000 or tetrahydrofurfuryl alcohol PEG ether (glycofurol, available commercially from BASF under the trade name Tetraglycol); surfactants, such as, sodium lauryl sulfate, oleic acid, linoleic acid, monoolein, lecithin, lysolecithin, deoxycholate, taurodeoxycholate, glycochenodeoxycholate, polyoxyethylene X-lauryl ether, where X is from 9 to 20, sodium tauro-24,25-dihydrofusidate, polyoxyethylene ether, polyoxyethylene sorbitan esters, p-t-octylphenoxypolyoxyethylene, N-lauryl-β-D-maltopyranoside, 1-dodecylazacycloheptane-2-azone; amides, such as, 2-pyrrolidone, 2-piperidone, caprolactam, N-alkylpyrrolidone, N-hydroxyalkylpyrrolidone, N-alkylpiperidone, N-alkylcaprolactam, dimethylacetamide, and polyvinylpyrrolidone; esters, such as, ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, β-butyrolactone and isomers thereof; and other solubilizers known in the art, such as dimethyl acetamide, dimethyl isosorbide (Arlasolve DMI (ICI)), N-methylpyrrolidones (Pharmasolve (ISP)), monooctanoin, and diethylene glycol monoethyl ether (available from Gattefosse under the trade name Transcutol).

Preferred additional solubilizers include triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-1000, PEG 300, PEG 400, Transcutol, and dimethyl isosorbide, sorbitol, glycerol, triacetin, glycofurol and propylene glycol. Typically, the solubilizer, if present, is present in an amount of from about 0.1% (w/v) to about 50% (w/v), from about 1% (w/v) to about 40% (w/v) or from about 2% (w/v) to about 25% (w/v). In addition, the liquid pharmaceutical composition can comprise water, for example, from about 2% (v/v) to about 99% (v/v), from about 10% (v/v) to about 95% (v/v), or from about 20% (v/v) to about 90% (v/v), of the liquid composition.

As discussed, the composition can comprise a preservative. In addition or in the alternative, the composition can be sterilized. Sterilization can be achieved by filter sterilization, autoclaving, exposure to ionizing radiation, for example, gamma radiation, UV irradiation, and chemical sterilization. In one embodiment, the sterile composition has a sterility assurance level of at least about $10^3$. The resulting liquid compositions preferably are stable at room temperature, such that less than 5%, 4%, 3%, 2% or 1% by weight of the therapeutic agent degrades after storage for 30 days, or more preferably 6 months, at 20° C.

In addition, the formulations may also include a sweetener or flavoring agent. Exemplary sweeteners or flavoring agents include, for example, acacia syrup, acesulfame potassium, anethole, anise oil, aromatic elixir, aspartame, benzaldehyde, benzaldehyde elixir, cyclodextrins, caraway, caraway oil, cardamom oil, cardamom seed, cardamom spirit, cardamom tincture, cherry juice, cherry syrup, cinnamon, cinnamon oil, cinnamon water, citric acid, citric acid syrup, clove oil, cocoa, cocoa syrup, coriander oil, dextrose, eriodictyol, eriodictyol fluid extract, eriodictyol syrup, aromatic, ethylacetate, ethyl vanillin, fennel oil, ginger, ginger fluid extract, ginger oleoresin, glucose, sugar, maltodextrin, glycerin, glycyrrhiza, glycyrrhiza elixir, glycyrrhiza extract, glycyrrhiza extract pure, glycyrrhiza fluid extract, glycyrrhiza syrup, honey, isoalcoholic elixir, lavender oil, lemon oil, lemon tincture, maltodextrin, maltose, mannitol, methyl salicylate, menthol, nutmeg oil, orange bitter, elixir, orange bitter, oil, orange flower oil, orange flower water, orange oil, orange peel, bitter, orange peel sweet, tincture, orange spirit, orange syrup, peppermint, peppermint oil, peppermint spirit, peppermint water, phenylethyl alcohol, raspberry juice, raspberry syrup, rosemary oil, rose oil, rose water, saccharin, saccharin calcium, saccharin sodium, sarsaparilla syrup, sarsaparilla compound, sorbitol solution, spearmint, spearmint oil, sucrose, sucralose, syrup, thyme oil, tolu balsam, tolu balsam syrup, wintergreen oil, vanilla, vanilla tincture, vanillin, wild cherry syrup, xylitol, or combinations thereof.

In addition, the formulations optionally can contain a taste masking agents. Exemplary masking agents include, for example, cyclodextrins, cyclodextrin emulsions, cyclodextrin particles, cyclodextrin complexes, or combinations thereof.

The foregoing list of excipients and additives is by no means complete, and it is understood that a person of ordinary skill in the art can choose other excipients and additives from the GRAS (generally regarding as safe) list of chemicals used in pharmaceutical preparations and those that are currently allowed in topical and parenteral formulations.

Exemplary liquid compositions of the invention contain, for example, the active ingredient (for example, midazolam), 40% (v/v) to 70% (v/v) methoxy-polyethylene glycol (for example, mPEG 350), 0% (v/v) to 20% (v/v) polyethylene glycol (for example, PEG 400), 0% (v/v) to 10% (v/v) propylene glycol, and 0% (v/v) to 5% (v/v) ethanol. Other exemplary liquid compositions of the invention contain, for example, the active ingredient dissolved in 50% (v/v) to 70% (v/v) mPEG 350, 1% (v/v) to 4% (v/v) propylene glycol, and 1% (v/v) to 4% (v/v) ethanol.

It is understood that the choice and amounts of each of the therapeutic agents, alkoxy-polyethylene glycol and other excipients combined to produce the compositions of the invention will depend upon the ultimate use of the composition, and the intended therapy and mode of administration. When the liquid compositions ultimately are administered to a patient, the amount of a given excipient, unless the circumstances dictate otherwise, preferably is limited to a bioacceptable amount, which is readily determined by one of skill in the art. Furthermore, it is understood that the liquid compositions of the invention can be formulated using techniques known to those skilled in the art. A thorough discussion of formulations and the selection of pharmaceutically acceptable carriers, stabilizers, etc. can be found, for example, in *Remington's Pharmaceutical Sciences* (18$^{th}$ Ed.), Mack Publishing Company, Eaton, Pa.

Although the therapeutic agent and the alkoxy-polyethylene glycol are combined in the liquid formulations of the invention, they are not covalently linked to one another. In certain embodiments, the liquid formulations of the invention are free or are substantially free of chitosan. In certain embodiments, the compositions of the invention may be prepared in a powder form.

II Modes of Administration and Pharmacokinetics

The compositions of the invention are particularly useful in delivering one or more therapeutic agents to a mucosal membrane or the skin of a mammal, for example, a human. The mucosal membrane to which the pharmaceutical preparation of the invention is administered may be any mucosal membrane of the mammal to which the therapeutic agent is to be applied, for example, the nose (for example, via a nasal membrane), vagina, eye (for example, via an ocular membrane), ear (for example, via a tympanic membrane), mouth (for example, via the buccal membrane), lungs (for example, via the pulmonal membrane), or rectum (for example, via the rectal membrane). The compositions are particularly useful in delivering a therapeutic agent to the mucosa of the nose, mouth (buccal, gingual, sublingual or to the hard palate), or the vagina.

It is understand that the compositions of the invention are particularly useful in the intranasal delivery of a therapeutic agent. When the composition is applied to the nasal mucosa, the volume of the pharmaceutical composition applied typically is in the range of 1-1000 µL, preferably not more than 700 µL, more preferably 50-150 µL per nostril, and most preferably about 100 µL/nostril.

It is understood that when administered intranasally, the compositions are delivered via a spray device that produces a plume of spray droplets that contact the nasal mucosa. It is contemplated that the compositions can be delivered using commercially available spray devices available from, for example, Pfeiffer of America, Princeton, N.J.; Valois of America, Inc., Greenwich, Conn.; or Becton Dickinson, Franklin Lakes, N.J. Furthermore, these devices are easily operable by the patient or care giver, and leave little or no residual formulation in the device after use.

Such devices can be filled with single or multi-dose amounts of the desired formulation. The container holding the pharmaceutical composition and its sealing means are sterilizable. At least the parts of the device that are in contact with the pharmaceutical composition should be constructed and assembled in a configuration that can be sterilized. Exemplary delivery devices with one or more unit-dose(s) are described, for example, in U.S. Pat. Nos. 4,946,069; 5,307,953; 6,948,492; and 6,446,839. Individual devices can be packaged, sterilized and shipped; alternatively, entire shipping and storage packages can be sterilized at once, and the devices removed individually for dispensing, without affecting the sterility of the remaining units.

The mucosal epithelium in the nasal cavity is covered with many hair-like cilia that provide an important defense mechanism against inhaled dust, allergens and microorganisms. The normal half-time for non-absorbed substances administered to the nasal cavity is about 15 minutes due to the mucociliary clearance removing foreign particles and excess mucus toward the pharynx. For this reason it is preferred that the absorption occurs rapidly and preferably within 0.5 to 20 minutes. However, in the current invention due to bioadhesive properties of the invention, the preferred absorption may occur within 0.5 to 300 minutes (e.g., for vaccines and biologicals), preferably between 0.5 to 60 minutes (e.g., for large molecules) and more preferably between 0.5 and 20 minutes, for example, within 2, 3, 4, 5, 10, 15 or 20 minutes post administration. The composition can be formulated so that upon administration to a subject, for example, via intranasal administration to the subject, the therapeutic agent has a peak concentration ($T_{max}$) in the blood of the subject within 30, 25, 20, 15, 10 8, 5, 3 or 2 minutes after administration of the therapeutic agent.

In addition to administration to humans, the compositions of the invention can be used to deliver the therapeutic agent to an animal, for example: pets, for example, dogs, cats, rabbits, and guinea pigs; and farm animals, for example, horses, sheep, pigs, cattle, and chickens.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Except where indicated otherwise, the order of steps or order for performing certain actions are immaterial so long as the invention remains operable. Moreover, unless otherwise noted, two or more steps or actions may be conducted simultaneously.

EXAMPLES

The invention is explained in more detail with reference to the following Examples, which are to be considered as illustrative and not to be construed so as to limit the scope of the invention as set forth in the appended claims.

Example 1

Exemplary Lorazapam Containing Formulation

In this Example, 10 mg lorazepam is dissolved in 2 mL of mPEG 350 using ultrasound to obtain a solution containing 5 mg/mL of lorazepam. 50 μL of the resulting composition is administered into each nasal cavity of male New Zealand White rabbits held in a supine position during, and then one minute after application. An Eppendorf pipette is used for each application. After administration, blood samples then are harvested from a marginal ear vein at 0, 2, 5, 10, 15, 30 and 60 minutes, and the lorazepam concentration determined by high performance liquid chromatography (HPLC). The pharmacokinetics of lorazepam delivery via intranasal administration can then be compared with the pharmacokinetics of lorazepam delivery by intravenous administration. It is contemplated that the pharmacokinetics of the intranasally administered lorazepam will be comparable to those of the intravenously administered lorazepam.

Example 2

Exemplary Midazolam Containing Formulation

In this Example, 10 mg of midazolam is dissolved in 2 mL of mPEG 350 using ultrasound to obtain a solution containing 5 mg/mL midazolam. 50 μL of the resulting composition is then administered into each nasal cavity of male New Zealand White rabbits, held in a supine position during, and then one minute after application. After administration, blood samples then are harvested from a marginal ear vein at 0, 2, 5, 10, 15, 30 and 60 minutes, and the midazolam concentration determined by HPLC. The pharmacokinetics of midazolam delivery via intranasal administration can then be compared with the pharmacokinetics of midazolam delivery by intravenous administration. It is contemplated that the pharmacokinetics of the intranasally administered midazolam will be comparable to those of the intravenously administered midazolam.

Example 3

Pharmacokinetics of Exemplary Midazolam Formulations

This Example describes a variety of formulations containing methoxy-polyethylene glycol that demonstrate comparable pharmacokinetic properties to a control formulation containing polyethylene glycol and propylene. In addition to having comparable pharmacokinetic properties, the methoxy-polyethylene glycol formulations had a lower viscosity than the control formulation.

Table 1 lists the composition of a first test formulation, Table 2 lists the composition of a second test formulation, and Table 3 lists the composition of a control formulation.

TABLE 1

Test Formulation 1 Containing 50 mg/mL Midazolam base

| Component | Percent of Final (% v/v) |
|---|---|
| mPEG 350 | 47 |
| PEG 400 | 18 |
| Propylene Glycol | 5 |
| Ethanol | 7 |
| Water | 21 |

TABLE 2

Test Formulation 2 Containing 50 mg/mL Midazolam base

| Component | Percent of Final (% v/v) |
|---|---|
| mPEG 350 | 47 |
| PEG 400 | 18 |
| Propylene Glycol | 10 |
| Polysorbate 80 | 0.1 |
| Water | 22 |

TABLE 3

Control Containing 50 mg/mL Midazolam base

| Component | Percent of Final (% v/v) |
|---|---|
| PEG 400 | 18 |
| Propylene Glycol | 78 |
| Butylatedhydoxytoluene | 0.01 |

Each of the test and control formulations contained 50 mg/mL midazolam. Once made, 5 mg of midazolam in 0.1 mL was delivered intranasally to the right nostril of each dog (3 dogs per set) for each formulation in a cross over manner. Blood was harvested from the dogs predose and at 0.03, 0.08, 0.16, 0.25, 0.5, 0.75, 1, 2, and 4 hours after administration, and the concentration of midazolam in the blood measured by HPLC. The pharmacokinetic properties are summarized in Table 4.

TABLE 4

Pharmacokinetic Properties

| Formulation | $T_{max}$ (hr) | $C_{max}$ (ng/mL) | $AUC_{last}$ (hr*ng/mL) | $AUC_{INF}$ (hr*ng/mL) |
|---|---|---|---|---|
| Test Formulation 1 | 0.11 ± 0.05 | 2220 ± 289 | 506 ± 94 | 508 ± 95 |
| Test Formulation 2 | 0.05 ± 0.03 | 1880 ± 682 | 399 ± 75 | 403 ± 76 |
| Control Formulation | 0.07 ± 0.03 | 2350 ± 796 | 506 ± 72 | 509 ± 71 |

In Table 4, Cmax refer to the maximum plasma concentration, $T_{max}$ refers to the time to reach $C_{max}$, $AUC_{last}$ refers to area under the concentration curve from time zero to the last measurable plasma concentration, and $AUC_{INF}$ refers to the area under the concentration curve from time zero to infinity.

The results demonstrate that the test formulations, when administered intranasally to the dogs, produced comparable pharmacokinetics to the control formulation. The test formulations, however, had a lower viscosity than the control formulations. Lower viscosity correlates with better spray pattern characteristics.

Example 4

Additional Exemplary Methoxy-Polyethylene Glycol Containing Formulations

This example describes the benefit of incorporating methoxy-polyethylene glycol into certain intranasal formulations. Table 5 describes a formulation containing methoxy-polyethylene glycol and PEG 400, Table 6 describes a formulation containing methoxy-polyethylene glycol without PEG 400, Table 7 describes a formulation containing methoxy-polyethylene glycol without PEG 400 (with reduced ethanol), and Table 8 describes a control formulation containing PEG 400 but no methoxy-polyethylene glycol.

TABLE 5

| Component | Viscosity (cP) | % (w/w) |
| --- | --- | --- |
| Propylene glycol | 40 | 5 |
| PEG 400 | 80 | 18 |
| mPEG 350 | 29 | 47 |
| Ethanol | — | 6 |
| Water | 1 | 18 |
| Midazolam | — | 7 |

TABLE 6

| Component | Viscosity (cP) | % (w/w) |
| --- | --- | --- |
| Propylene glycol | 40 | 2 |
| mPEG 350 | 29 | 64 |
| Ethanol | — | 5 |
| Water | 1 | 23 |
| Midazolam | — | 7 |

TABLE 7

| Component | 75 mg Midazolam/ dose (% w/w) | 50 mg Midazolam/ dose (% w/w) | 25 mg Midazolam/ dose (% w/w) |
| --- | --- | --- | --- |
| MPEG 350 | 64.8 | 64.8 | 64.8 |
| Propylene glycol | 2.0 | 2.0 | 2.0 |
| Ethanol | 2.5 | 2.5 | 2.5 |
| Water | 23.7 | 26.0 | 28.3 |
| Phenethyl Alcohol | 0.025 | 0.025 | 0.025 |
| Midazolam | 6.9 | 4.6 | 2.3 |

TABLE 8

Control Formulation (Without Methoxy-polyethylene Glycol)

| Component | Viscosity (cP) | % (w/w) |
| --- | --- | --- |
| PEG 400 | 89 | 19 |
| Propylene Glycol | 40 | 76 |
| Butylatedhydroxytoluene | — | 0.01 |
| Midazolam | — | 5 |

The formulation of Table 5 was prepared by mixing the propylene glycol, PEG 400, mPEG 350, and ethanol. The midazolam was then added to the mixture, and then after the midazolam had dissolved following mixing the water was added to the formulation. The formulations in Tables 6 and 7 were prepared as follows. The midazolam was weighed in a container and the ethanol was added to wet the active ingredient. After mixing, about 65% of the mPEG 350 was added, and the resulting mixture mixed for 2 minutes. Thereafter, the additional organic phase was added. The remaining 35% of the mPEG 350 was mixed with water, and the diluted mPEG 350 then was gradually added with mixing to the midazolam solution until a clear solution was produced. The viscosity of the resulting formulations and spray patterns were tested.

The viscosity of the resulting formulations was tested at 25° C. using a viscometer (Brookfield DV-II PRO). The viscosity of the control formulation without methoxy-polyethylene glycol (Table 8) was found to be about 42 cP, whereas the viscosity of the test formulation of Table 5 was found to be about 30 cP, and the viscosity of the test formulation of Table 6 was found to be about 23 cP. The reduced viscosity of the test formulations relative to the control formulation permitted the creation of more reproducible spray patterns.

The spray patterns produced by the two test formulations of Tables 5 and 6 were tested using a Proveris spray view instrument. The resulting parameters of the resulting spray patterns were found to be more reproducible as the viscosity of the formulation decreased.

In addition, 100 µL of placebo formulations (no midazolam) corresponding to the formulations set forth in Tables 7 and 8 were administered intranasally to three healthy test subjects using a commercially available spray device from Pfeiffer. The placebo formulation corresponding to Table 7 containing methoxy-polyethylene glycol had a less noticeable taste relative to the placebo formulation corresponding to Table 8.

These collective results demonstrate that mPEG 350 is a suitable excipient for nasal administration, for example, with midazolam.

Example 5

Sprayability of Methoxy-Polyethylene Glycol Containing Formulations

This Example demonstrates that methoxy-polyethylene glycol-based formulations produce superior spray flumes relative to polyethylene glycol. Solutions containing 100% methoxy-polyethylene glycol 350 (MPEG 350) from Sigma-Aldrich Chemie GmbH (St. Louis, Mo., USA) and 100% polyethylene glycol 300 (PEG 300) from Croda Chemicals Europe Ltd. (Goole, UK) were placed into Pfeiffer 20 mL bottles (Pfeiffer 34473) and attached to certain pumps from Valois or Pfeiffer (see Table 8). Each spray device was placed 25 cm under a sheet of absorbent paper and the sprayability was measured as the diameter across of the paper wetted by the resulting spray. The results are summarized in Table 9.

TABLE 9

| Pump Type | Formulation | Spray diameter (cm) |
| --- | --- | --- |
| Pfeiffer 71514 | PEG 300 | 2.0-3.2 cm |
| Pfeiffer 71514 | mPEG 350 | 22-26 cm |
| Valois VP6/100 | PEG 300 | 5.0-7.5 cm |
| Valois VP6/100 | mPEG 350 | 15-21 cm |

The results show that there is a clear difference in the sprayability of mPEG 350 compared with PEG 300. The required spray angle is not achieved using PEG 300, whereas a clinically relevant spray-angle can be achieved using mPEG 350.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A liquid pharmaceutical composition formulated for intranasal administration, comprising:
   i) midazolam or a pharmaceutically salt thereof; and
   ii) a methoxy-polyethylene glycol selected from the group consisting of methoxy-polyethylene glycol 350 and methoxy-polyethylene glycol 550.

2. The pharmaceutical composition of claim 1, further comprising propylene glycol.

3. The pharmaceutical composition of claim 2, further comprising water.

4. The pharmaceutical composition of claim 1, wherein the methoxy-polyethylene glycol is methoxy-polyethylene glycol 350.

5. The pharmaceutical composition of claim 3, wherein the methoxy-polyethylene glycol is methoxy-polyethylene glycol 350.

6. The pharmaceutical composition of claim 1, further comprising polyethylene glycol.

7. The pharmaceutical composition of claim 5, further comprising polyethylene glycol.

8. The pharmaceutical composition of claim 1, further comprising ethyl alcohol.

9. The pharmaceutical composition of claim 6, wherein the polyethylene glycol is polyethylene glycol 400.

10. The pharmaceutical composition of claim 7, wherein the polyethylene glycol is polyethylene glycol 400.

11. The pharmaceutical composition of claim 1, wherein the midazolam is present in a concentration from 0.001% (w/v) to 20% (w/v).

12. The pharmaceutical composition of claim 1, further comprising water.

13. The pharmaceutical composition of claim 10, wherein the midazolam is present in a concentration from 0.001% (w/v) to 20% (w/v).

14. The pharmaceutical composition of claim 9, wherein the methoxypolyethylene glycol is methoxy-polyethylene glycol 350.

15. A method of administering midazolam to a mammal, the method comprising administering a pharmaceutical composition to a mucosal surface of the mammal, the pharmaceutical composition comprising:
   midazolam or a pharmaceutically acceptable salt thereof; and
   a methoxy-polyethylene glycol selected from the group consisting of methoxy polyethylene glycol 350 and methoxy-polyethylene glycol 550.

16. The method of claim 15, wherein the mucosal surface is a nasal membrane, buccal membrane, pulmonal membrane, ocular membrane, or rectal membrane.

17. The method of claim 15, wherein the mucosal surface is a nasal membrane.

18. The method of claim 15, wherein the midazolam has a peak concentration ($T_{max}$) in the blood of the mammal within 30 minutes after administration of the midazolam.

19. The method of claim 15, wherein the midazolam has a peak concentration ($T_{max}$) in the blood of the mammal within 15 minutes after administration of the midazolam.

20. The method of claim 15, wherein the pharmaceutical composition is administered in a volume of 50 µl to 300 µl.

21. The method of claim 15, wherein the mammal is a human.

* * * * *